United States Patent [19]

Gander

[11] 4,323,581

[45] Apr. 6, 1982

[54] METHOD OF TREATING CARCINOGENESIS

[75] Inventor: Robert J. Gander, Whitehouse, N.J.

[73] Assignee: Johnson & Johnson, New Brunswick, N.J.

[21] Appl. No.: 929,094

[22] Filed: Jul. 31, 1978

[51] Int. Cl.³ .......................................... A61K 31/165
[52] U.S. Cl. ..................................................... 424/324
[58] Field of Search ......................................... 424/324

[56] References Cited

U.S. PATENT DOCUMENTS 4,108,880  8/1978  Gander et al. .................. 260/410.5

*Primary Examiner*—Jerome D. Goldberg
*Attorney, Agent, or Firm*—Irving Newman

[57] ABSTRACT

Periodic administration of N-(4-hydroxyphenyl)-all-trans-retinamide has been found to prevent breast cancer in mammals.

10 Claims, 2 Drawing Figures

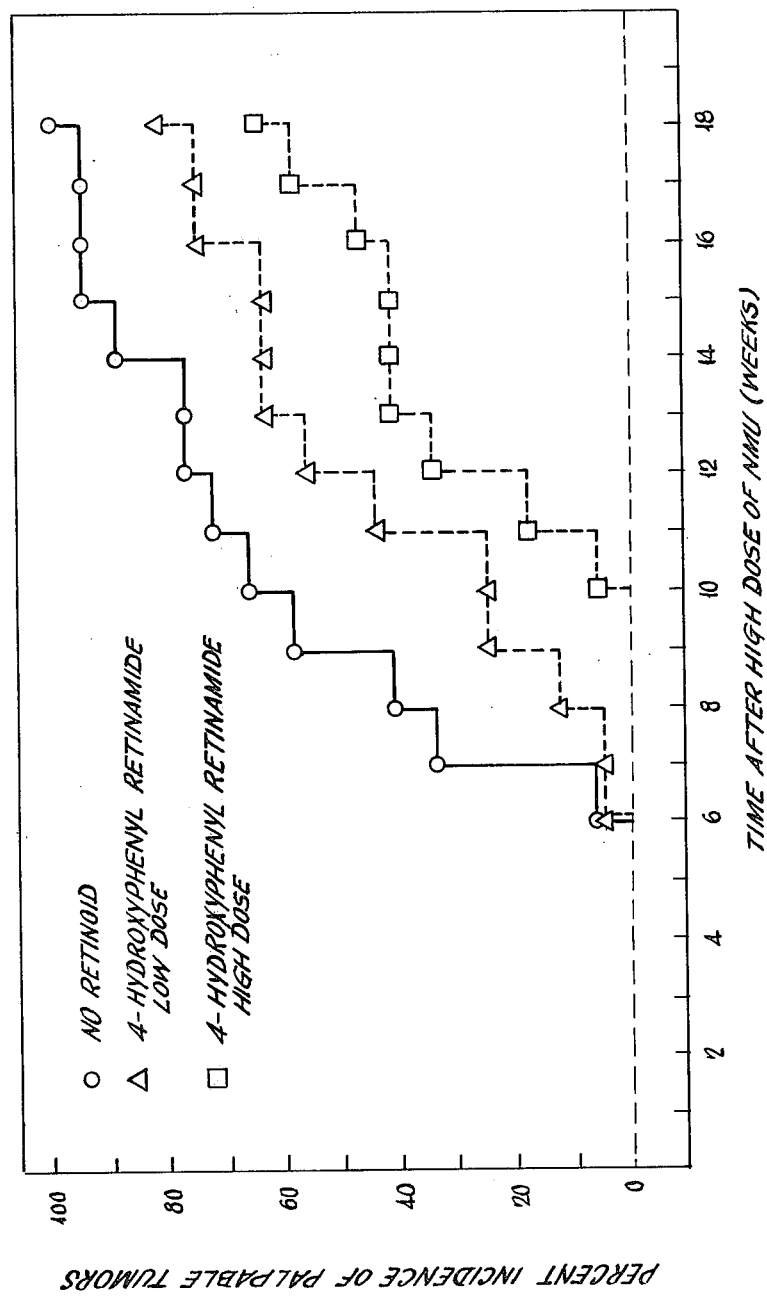

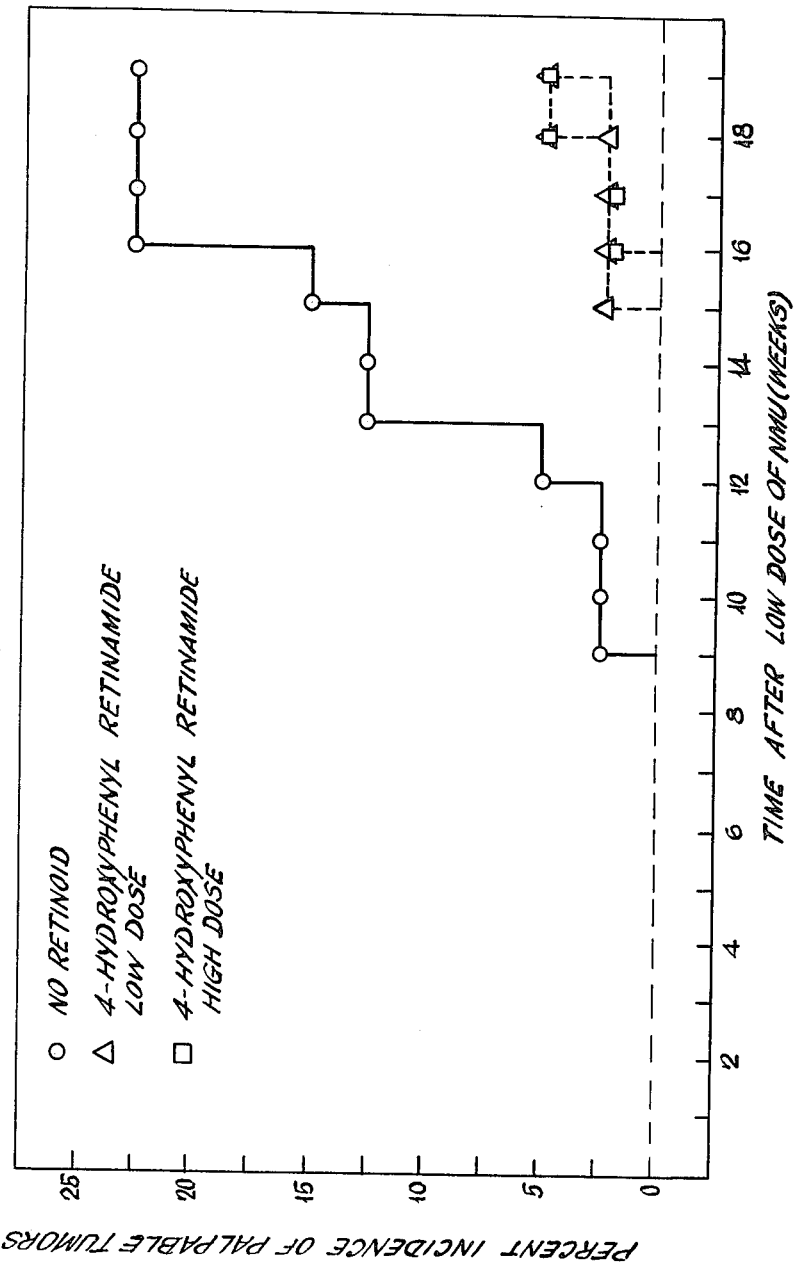

METHOD OF TREATING CARCINOGENESIS

TECHNICAL FIELD

This invention relates to the use of chemicals to prevent the development of cancer in mammals. More particularly, it relates to the use of a retinoid, N-(4-hydroxyphenyl)-all-trans-retinamide, to prevent certain forms of epithelial cancer.

BACKGROUND ART

As pointed out in a paper entitled "Approaches to Prevention of Epithelial Cancer During The Preneoplastic Period", *Cancer Research*, 36 (July, 1976), 2699–2702, presented at a Conference on "Early Lesions and The Development of Epithelial Cancer" (National Cancer Institute, Oct. 21–23, 1975), the death rates for several common forms of epithelial cancer either increased or showed no decrease during the 20-year period from 1950 to 1970. These epithelial cancer sites included the lung and pancreas in both men and women, the colon and bladder in men, the breast and ovary in women. The conventional clinical approach that has been followed with most epithelial cancer has been to wait until the patient has invasive disease and then treat this disease with cytotoxic chemotherapy, surgery, or radiation. None of these modalities has been overwhelmingly successful for the treatment of all types of epithelial cancer, in spite of some advances that have occurred.

Accordingly, it has been suggested that an alternative approach to the problem of epithelial cancer is to consider the disease as a process which takes many years to reach its final, invasive stage in man and which might be controlled by physiological or pharmacological mechanisms during its early stages, with the goal of prevention of end-stage, invasive, terminal disease.

Retinoids play an essential role in controlling the normal differentiation of epithelial tissues and are therefore important for controlling premalignant epithelial cell differentiation. It has even been found that retinoids can cause cellular repair of hyperplastic and anaplastic lesions caused by chemical carcinogens. Moreover, retinoid deficiency has been shown, in experimental animals, to enhance susceptibility to chemical carcinogenesis. Indeed, retinoids are essential for the normal cellular differentiation of epithelia that account for more than half of the total primary cancer in both men and women. These epithelia include those of the bronchi and trachea, stomach, intestine, uterus, kidney and bladder, testis, prostate, pancreatic ducts, and skin. In the absence of retinoids in the diet, normal cellular differentiation does not occur in these epithelia.

However, natural retinyl esters, such as retinyl acetate and retinyl palmitate, as well as retinoic acid, have been found to be too toxic at high dosage levels to be of practical value for cancer prevention in higher mammals. Progress has been made recently in identifying synthetic retinoids, for example 13-cis-retinoic acid, that are considerably less toxic than retinoic acid or the natural retinyl esters, and are also more potent in preventing chemical carcinogenesis. See "13-cis-Retinoic Acid:Inhibitor of Bladder Carcinogenesis in the Rat", *Science*, Feb. 4, 1977, Volume 195, pp 487–489 as well as "13-cis-Retinoic Acid: Inhibition of Bladder Carcinogenesis Induced in Rats by N-Butyl-N-(4-hydroxybutyl) nitrosamine", *Science, Nov.* 18, 1977, Volume 198, pages 743–744. 13-cis-retinoic acid, however, has not been found to be particularly effective against breast cancer in the rat model discussed hereinafter.

Recent developments in this field, as summarized above, are also discussed in an article entitled "Prevention of Chemical Carcinogenesis by Vitamin A and its Synthetic Analogs (Retinoids)", *Federation Proceedings*, 35, (May 1, 1976), 1332–1338, in which it is noted that it still remains a goal to find, for practical application to man and other mammals, highly effective synthetic retinoids that also have low toxicity and a high degree of tissue specificity against cancer at any particular organ site. See also the articles in the Fall, 1977, issue of *The Southern Research Institute Bulletin* (Volume 30, Number 2), pages 3–9 ("CHEMOPREVENTION OF CANCER-Steps Leading to Some Malignancies May Be Reversible" and "How Do Retinoids Work? Studies on Retinoic Acid-Binding Protein"). Other recent publications of interest in this field include "Biological Activity and Metabolism of the Retinoid Axerophthene (Vitamin A Hydrocarbon)", *Cancer Research* 38, 1734–1738, June 1978; and "Retinoids and Cancer Prevention: The importance of the Terminal Group of the Retinoid Molecule In Modifying Activity and Toxicity" in *Carcinogens: Identification and Mechanism of Action*, A. C. Griffin & C. R. Shaw, Editors, N.Y. Raven Press, 1978 (in Press).

In prior U.S. patent application Ser. No. 628,177, filed Nov. 3, 1975, now U.S. Pat. No. 4,108,880, N-(4-hydroxyphenyl)-all-trans-retinamide is disclosed as being a good ultraviolet absorber that does not have the irritating effect on skin that would be expected from the use of sunscreening amounts of retinoic acid. This compound is claimed in a divisional of the above-identified application, U.S. patent application Ser. No. 906,168, filed May 15, 1978.

DISCLOSURE OF INVENTION

It has now been found that N-(4-hydroxyphenyl)-all-trans-retinamide,

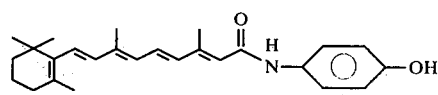

has an unusually desirable combination of properties-low systemic toxicity, good effectiveness in preventing epithelial cancer in mammals at reasonable dose levels, and adequate target specificity in concentrating at the breast. It is expected that it will also concentrate at one or more other common sites of epithelial cancer such as the bladder, colon, lung and pancreas.

BEST MODE FOR CARRYING OUT THE INVENTION

A suitable method for preparing N-(4-hydroxyphenyl)-all-trans-retinamide is described in Example 1 below.

EXAMPLE 1

A solution of retinoyl chloride was prepared by magnetically stirring 3.00 g. of all-trans-retinoic acid and 0.92 g. of phosphorous trichloride for 2.25 hours in 50 ml. of dry benzene. During 21 minutes, the retinoyl chloride solution was then added to a solution of 5.46 g. of 4-aminophenol in 16 ml. of anhydrous N,N-dimethylformamide and 2 ml. of anhydrous ethyl ether, while stirring under a nitrogen atmosphere and cooling in an ice bath. Stirring was then continued for three hours at room temperature and for an hour more at 50° C.

The reaction mixture was diluted with 150 ml. of ethyl ether. The ether solution was extracted with two 25-ml. portions of cold 5% hydrochloric acid and then was washed with four 25-ml. portions of cold water. After the washed solution was dried over sodium sulfate, the solvent was evaporated, leaving a dark-yellow solid. The solid was recrystallized first from methanol (6 ml. per gram), then from 1:1.7 chloroform-n-hexane (8 ml. per gram). The product had a melting point of 159°–160° C. The proton magnetic resonance spectrum of the product was consistent with the structure with no extraneous resonances.

Anal. Calcd. for $C_{26}H_{33}NO_2$:C, 79.8; H, 8.49; N, 3.58. Found: C, 79.5; H, 8.67; N, 3.56.

In use for the prevention of carcinogenesis, the N-(4-hydroxyphenyl)-all-trans-retinamide is administered systemically, preferably orally, in a pharmaceutically acceptable vehicle compatible therewith at a dosage level effective to prevent or retard carcinogenesis but below that which would be toxic. The drug is administered at regular intervals, conveniently at meal times or once daily. It has been established that the $LD_{50}$ of the active compound (in Swiss mice) is 436 mg/kg when given interperitoneally and in excess of 400 mg/kg when given orally. On the other hand, oral doses of 32 and 64 mg/kg/day have been found to be very effective in preventing breast cancer in rats. It is believed that for other mammals, a suitable effective dosage level will be within the above range and, probably, lower doses will also prove efficaceous.

EXAMPLE 2

N-(4-hydroxyphenyl)-all-trans-retinamide was compared with retinoic acid in an in vitro screening model for identifying retinoids having activity in preventing carcinogenesis in epithelial tissue. The experimental method, which is described in *Experimental Lung Cancer:Intern'l Symp*, 575–82, 1974, involves reversal of keratinization in tracheal organ culture.

In brief summary, in the absence of retinoic acid or a synthetic retinoid having similar activity, the test organ culture of tracheal epithelium undergoes abnormal differentiation. Addition of small concentrations of retinoic acid (as low as $10^{-9}$M) will cause reversion to normal tracheal epithelium. Test compounds are compared in activity to retinoic acid or another active standard both as regards squamous metaplasia and keratin production, both of which are measures of abnormal development of the epithelial culture. The results, summarized in Table I below, show that the 4-hydroxyphenyl retinamide is at least as efficacious as retinoic acid at a concentration of $10^{-8}$M, and nearly as efficacious at $10^{-9}$M, although virtually inefficacious at $10^{-10}$M.

In carrying out the tests reported in Table I, all tracheas were cultured for the first 3 days in medium without retinoid. At this time, some tracheas were collected, while the rest were cultured for a further week in medium containing either no retinoid, or retinoid added at the concentrations shown. These tracheas were collected on the 10th day of culture. Cultures were graded as to the percentage of their total epithelium showing squamous metaplasia on eight cross sections from the middle of each trachea. If more than 40% of the total epithelial length was squamous, it was graded as having severe squamous metaplasia; between 10–40% was graded as marked; between 2–10% was graded as mild; and less than 2% was graded as minimal.

TABLE I

Reversal of Keratinized Squamous Metaplastic Lesions of Vitamin A Deficiency in Tracheal Organ Cultures Treated with Retinoids

| Treatment of Cultures (number of cultures) | | % of Cultures with Respective Amounts of Squamous Metaplasia | | | | | % of Cultures with Keratin and Keratohyaline Granules |
|---|---|---|---|---|---|---|---|
| | | None | Minimal | Mild | Marked | Severe | |
| No Retinoid, collected day 3 | (152) | 12 | 8 | 42 | 26 | 79 | 71 |
| No Retinoid, collected day 10 | (140) | 1 | 2 | 11 | 50 | 34 | 95 |
| Retinoic Acid | | | | | | | |
| $10^{-8}$ M | (26) | 27 | 49 | 23 | 0 | 0 | 0 |
| $10^{-9}$ M | (134) | 16 | 37 | 32 | 12 | 2 | 3 |
| $10^{-10}$ M | (47) | 9 | 4 | 43 | 17 | 28 | 32 |
| 4-Hydroxyphenyl Retinamide | | | | | | | |
| $10^{-8}$ M | (10) | 20 | 80 | 0 | 0 | 0 | 0 |
| $10^{-9}$ M | (10) | 20 | 20 | 30 | 0 | 30 | 40 |
| $10^{-10}$ M | (8) | 0 | 0 | 12 | 75 | 12 | 100 |

EXAMPLE 3

On the basis of the encouraging results summarized in the foregoing example, N-(4-hydroxyphenyl)-all-trans-retinamide was compared to retinyl acetate in the experimental assay for efficacy against rat breast cancer described in *Nature* Vol. 267, pp 620–621 (June 16, 1977), which measures the ability to inhibit mammary carcinogenesis induced by N-methyl-N-nitrosourea (MNU). The test conditions and results after 10½ weeks of testing are set forth in Table II. The results of further extension of the tests, comparing the 4-hydroxyphenyl retinamide only to placebo, after 18 weeks with high dose MNU and 21 weeks with low dose MNU, are set forth in Table III. The results using these two different levels of MNU and two dietary levels of retinoid are shown graphically in FIGS. 1 and 2 after 18 weeks of testing.

Not only is the 4-hydroxyphenyl retinamide substantially as efficacious as retinyl acetate, it is also less toxic. Of particular importance is the fact that, unlike the natural retinyl esters, this retinamide does not accumulate in the liver in appreciable amounts, thus avoiding the hepatotoxicity associated with prolonged use of the natural esters.

TABLE II

Relative Effects of Retinyl Acetate and 4-Hydroxyphenyl Retinamide
On N-Methyl-N-Nitrosourea (MNU) - Induced Mammary Cancer (73 days)

| Carcinogen | Retinoid | Mammary Tumor Incidence | |
|---|---|---|---|
| Saline | Placebo | 0/10 | (0%) |
| Saline | Retinyl Acetate, 328 mg/kg diet | 0/10 | (0%) |
| Saline | Retinyl Acetate, 656 mg/kg diet | 0/10 | (0%) |
| Saline | 4-Hydroxyphenyl Retinamide, 391 mg/kg diet | 0/10 | (0%) |
| Saline | 4-hydroxyphenyl Retinamide, 782 mg/kg diet | 0/10 | (0%) |
| MNU, high dose | Placebo | 14/17 | (82%) |
| MNU, high dose | Retinyl Acetate, 328 mg/kg diet | 5/19 | (26%) |
| MNU, high dose | Retinyl Acetate, 656 mg/kg diet | 4/17 | (24%) |
| MNU, high dose | 4-Hydroxyphenyl Retinamide, 391 mg/kg diet | 5/16 | (31%) |
| MNU, high dose | 4-Hydroxyphenyl Retinamide, 782 mg/kg diet | 0/17 | (0%) |
| MNU, low dose | Placebo | 1/40 | (2.5%) |
| MNU, low dose | Retinyl Acetate, 328 mg/kg diet | 0/39 | (0%) |
| MNU, low dose | Retinyl Acetate, 656 mg/kg diet | 0/40 | (0%) |
| MNU, low dose | 4-Hydroxyphenyl Retinamide, 391 mg/kg diet | 0/40 | (0%) |
| MNU, low dose | 4-Hydroxyphenyl Retinamide, 782 mg/kg diet | 0/39 | (0%) |

| | |
|---|---|
| Animals: | Female Sprague-Dawley rats obtained from ARS Sprague-Dawley. |
| Carcinogen: | Crystalline MNU. Rats received 2 I.V. injections at 50 and 57 days of age. High dose is 50 mg/kg; low dose 15 mg/kg. |
| Retinoids: | Retinoids were dissolved in solvent and blended into the diets. Rats were placed on diets 3 days after last MNU injection. |
| Retinoid Solvent: | 50 gm trioctanoin:ethanol (3:1), 0.05 ml Tenox 20, 0.05 ml DL-α-Tocopherol/kg Wayne lab meal. |
| Retinoid Placebo: | 50 gm retinoid solvent/kg diet. |

TABLE III

Effect of 4-Hydroxyphenyl Retinamide on N-Methyl-N-Nitrosourea
(MNU) - Induced Mammary Cancer

| Carcinogen | Retinoid | Mammary Tumor Incidence | | Total Number of Tumors |
|---|---|---|---|---|
| Saline | Placebo | 0/10 | (0%) | 0 |
| Saline | 4-Hydroxyphenyl Retinamide, 391 mg/kg diet | 0/10 | (0%) | 0 |
| Saline | 4-Hydroxyphenyl Retinamide, 782 mg/kg diet | 0/10 | (0%) | 0 |
| MNU, high dose | Placebo | 17/17 | (100%) | 85 |
| MNU, high dose | 4-Hydroxyphenyl Retinamide, 391 mg/kg diet | 13/16 | (81%) | 48 |
| MNU, high dose | 4-Hydroxyphenyl Retinamide, 782 mg/kg diet | 11/17 | (64%) | 37 |
| MNU, low dose | Placebo | 12/40 | (30%) | 13 |
| MNU, low dose | 4-Hydroxyphenyl Retinamide, 391 mg/kg diet | 5/40 | (12%) | 5 |
| MNU, low dose | 4-Hydroxyphenyl Retinamide, 782 mg/kg diet | 3/39 | (8%) | 4 |

| | |
|---|---|
| Animals: | Female Sprague-Dawley rats obtained from ARS Sprague-Dawley. |
| Carcinogen: | Crystalline MNU. Rats received 2 I.V. injections at 50 and 57 days of age. High dose is 50 mg/kg; low dose 15 mg/kg. Rats on high dose of MNU were sacrificed after 18 weeks. |
| Retinoids: | Retinoids were dissolved in solvent and blended into the diets. Rats were placed on diets 3 days after last MNU injection. |
| Retinoid Solvent: | 50 gm trioctanoin:ethanol (3:1), 0.05 ml Tenox 20, 0.05 ml DL-α-Tocopherol/kg Wayne lab meal. |
| Placebo: | 50 gm retinoid solvent/kg diet. |

Variations can, of course, be made without departing from the spirit and scope of the invention.

What is claimed is:

1. A method of treating carcinogenesis in epithelial tissue in a mammal in need of said treatment, which comprises periodically administering to the subject mammal an effective amount for treating carcinogenesis of N-(4-hydroxyphenyl)-all-trans-retinamide.

2. The method of claim 1 wherein said hydroxyphenyl retinamide is administered orally.

3. The method of claim 2 wherein said hydroxyphenyl retinamide is administered at least once daily.

4. The method of claim 3 wherein said hydroxyphenyl retinamide is administered in an amount up to about 65 mg/kg/day.

5. The method of claim 4 wherein said amount does not exceed about 35 mg/kg/day.

6. The method of claim 1 wherein said hydroxyphenyl retinamide is administered in an amount up to about 65 mg/kg/day.

7. The method of claim 6 wherein said amount does not exceed about 35 mg/kg/day.

8. The method of claim 1 wherein said epithelial tissue is breast tissue.

9. A composition for treating carcinogenesis in epithelial tissue comprising an effective amount for treating carcinogenesis of N-(4-hydroxyphenyl)-all-trans-retinamide in a pharmaceutically acceptable systemic vehicle compatible therewith.

10. The composition of claim 9 in oral dosage form.

* * * * *